United States Patent
Sun et al.

(10) Patent No.: US 7,825,261 B2
(45) Date of Patent: Nov. 2, 2010

(54) INDAZOLE COMPOUNDS

(75) Inventors: Chung-Ming Sun, Rancho Cucamonga, CA (US); Min-Liang Kuo, Taipei (TW)

(73) Assignee: National Taiwan University, Taipei (TW)

( * ) Notice: Subject to any disclaimer, the term of this patent is extended or adjusted under 35 U.S.C. 154(b) by 68 days.

(21) Appl. No.: 11/949,070

(22) Filed: Dec. 3, 2007

(65) Prior Publication Data

US 2008/0132501 A1 Jun. 5, 2008

Related U.S. Application Data

(60) Provisional application No. 60/873,041, filed on Dec. 5, 2006.

(51) Int. Cl.
 *C07D 231/56* (2006.01)
(52) U.S. Cl. .................. 548/361.1; 548/362.5
(58) Field of Classification Search ........... 514/406; 548/361.1, 362.5
See application file for complete search history.

(56) References Cited

U.S. PATENT DOCUMENTS 6,262,040 B1 * 7/2001 Marfat .................. 514/158
2004/0204409 A1 * 10/2004 Ando et al. ............. 514/235.2

FOREIGN PATENT DOCUMENTS

WO WO 2004094411 A1 * 11/2004
WO WO2005/105094 11/2005

OTHER PUBLICATIONS

Cited ref_11949070_STN preliminary search.*

Mills et al., "N,N-Bond-Forming Heterocyclization: Synthesis of 3-Alkoxy-2H-Indazoles," *J.Org Chem*, vol. 71, pp. 2687-2689 (2006).
Takami et al., "Design and Synthesis of Rho Kinase Inhibitors (I)," *Bioorg. Med. Chem*, vol. 12, pp. 2115-2137 (2004).
Curini et al., "Layered Zirconium Sulfophenyl Phosphonate as Heterogeneous Catalyst in the Synthesis of Pyrazoles and 4,5,6,7-Tetrahydro-1(2)H-indazoles," *Synlett*, No. 19, pp. 2927-2930 (2005).

* cited by examiner

*Primary Examiner*—Yong Chu
(74) *Attorney, Agent, or Firm*—Occhiuti Rohlicek & Tsao LLP

(57) ABSTRACT

This invention relates to indazole compounds of formula (I) or (II) shown below. Each variable in formula (I) or (II) is defined in the specification. These compounds can be used to treat cancer.

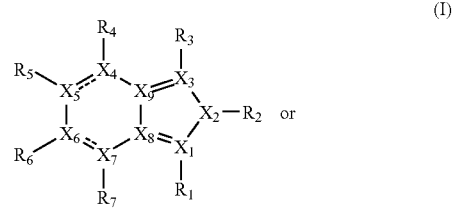

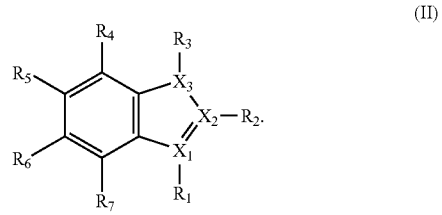

3 Claims, No Drawings

INDAZOLE COMPOUNDS

CROSS REFERENCE TO RELATED APPLICATION

Pursuant to 35 U.S.C. §119(e), this application claims priority to U.S. Provisional Application Ser. No. 60/873,041, filed Dec. 5, 2006, the content of which is incorporated herein by reference.

BACKGROUND

The role of lymphangiogenesis in promoting metastasis via the lymphatic system has been the subject of extensive research. Vascular endothelial growth factor receptor-3 (VEGFR-3) is a major mediator of lymphangiogenesis. VEGF-C and VEGF-D are two ligands for VEGFR-3. Both of them were shown to stimulate lymphangiogenesis in transgenic mice. Specifically, three cancer cell lines transfected with VEGF-C or VEGF-D were recently reported to exhibit increased tumor lymphangiogenesis and undergo lymphatic metastasis. Clinical studies also revealed that increased expression of VEGF-C was associated with lymph node metastasis in a variety of cancers in human. Thus, it is desirable to develop novel drugs that inhibit VEGFR-3 activities for use in treating cancer.

SUMMARY

This invention is based on the discovery that certain indazole compounds are effective in reducing metastasis and treating cancer by inhibiting VEGFR-3 activities.

In one aspect, this invention features indazole compounds of formula (I):

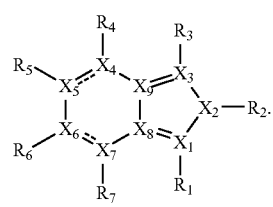

(I)

In this formula, each ≕ independently is a double bond or single bond; each of $X_1$, $X_2$, $X_3$, $X_4$, $X_5$, $X_6$, and $X_7$, independently, is C or N, provided that at least two of $X_1$, $X_2$, and $X_3$ are N; and that when $X_1$ is N, $R_1$ is deleted, when $X_3$ is N, $R_3$ is deleted, when $X_4$ is N, $R_4$ is deleted, when $X_5$ is N, $R_5$ is deleted, when $X_6$ is N, $R_6$ is deleted, and when $X_7$ is N, $R_7$ is deleted; each of $X_8$ and $X_9$, independently, is C or $N^+$; and each of $R_1$, $R_2$, $R_3$, $R_4$, $R_5$, $R_6$, and $R_7$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, CN, $NO_2$, $OR_a$, $COOR_a$, $OC(O)R_a$, $C(O)R_a$, $C(O)NR_aR_b$, $C(O)N(R_a)N(R_b)C(O)R_c$, $NR_aR_b$, $N(R_c)SO_2NR_aR_b$, $SO_2NR_aR_b$, or $SR_a$, in which each of $R_a$, $R_b$, and $R_c$, independently, is H, $C_1$-$C_{10}$ alkyl, $C_3$-$C_{20}$ cycloalkyl, $C_1$-$C_{20}$ heterocycloalkyl, aryl, or heteroaryl, or $R_a$ and $R_b$ together with the nitrogen atom to which they are attached form a $C_1$-$C_{20}$ heterocycloalkyl or heteroaryl.

Referring to formula (I), a subset of the indazole compounds described above are those in which each of $X_1$, $X_4$, $X_5$, $X_6$, $X_7$, $X_8$, and $X_9$, independently, is C and each of $X_2$ and $X_3$, independently, is N. In these compounds, $R_1$ can be H or $OR_a$; $R_2$ can be $C_3$-$C_{20}$ cycloalkyl, $C_1$-$C_{10}$ alkyl optionally substituted with aryl or $C_1$-$C_{20}$ heterocycloalkyl, or aryl optionally substituted with $C_1$-$C_{10}$ alkyl; and each of $R_4$, $R_5$, $R_6$, and $R_7$, independently, can be H, $C_1$-$C_{10}$ alkyl, $NR_aR_b$, $COOR_a$, $C(O)NR_aR_b$, $C(O)N(R_a)N(R_b)C(O)R_c$, or heteroaryl.

In another aspect, this invention features indazole compounds of formula (II):

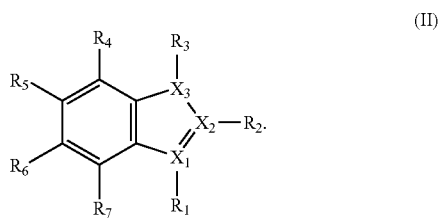

(II)

In this formula, each of $X_1$, $X_2$, and $X_3$, independently, is C or N, provided that at least two of $X_1$, $X_2$, and $X_3$ are N; and that when $X_1$ is N, $R_1$ is deleted, when $X_2$ is N, $R_2$ is deleted; and each of $R_1$, $R_2$, $R_3$, $R_4$, $R_5$, $R_6$, and $R_7$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, CN, $NO_2$, $OR_a$, $COOR_a$, $OC(O)R_a$, $C(O)R_a$, $C(O)NR_aR_b$, $C(O)N(R_a)N(R_b)C(O)R_c$, $NR_aR_b$, $N(R_c)SO_2NR_aR_b$, $SO_2NR_aR_b$, or $SR_a$, in which each of $R_a$, $R_b$, and $R_c$, independently, is H, $C_1$-$C_{10}$ alkyl, $C_3$-$C_{20}$ cycloalkyl, $C_1$-$C_{20}$ heterocycloalkyl, aryl, or heteroaryl, or $R_a$ and $R_b$ together with the nitrogen atom to which they are attached form a $C_1$-$C_{20}$ heterocycloalkyl or heteroaryl.

Referring to formula (II), a subset of the indazole compounds described above are those in which $X_1$ is C, each of $X_2$ and $X_3$, independently, is N, and each of $R_3$, $R_4$, $R_5$, $R_6$, and $R_7$, independently, is H, $C_1$-$C_{10}$ alkyl, $NR_aR_b$, $COOR_a$, $C(O)NR_aR_b$, $C(O)N(R_a)N(R_b)C(O)R_c$, or heteroaryl.

The term "compound" used herein includes both compounds and ions. For example, when $X_8$ or $X_9$ is $N^+$, the compound of formula (I) is a cation. The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH═CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention features a method for treating cancer. The method includes administering to a subject in need thereof an effective amount of one or more indazole compounds of formula (I) or (II) shown above. An example of cancer that can be treated by the indazole compounds of this invention is lung cancer. The term "treating" or "treatment" refers to administering one or more indazole compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

In addition, this invention encompasses a pharmaceutical composition that contains at least one of the above-mentioned indazole compounds and a pharmaceutically acceptable carrier.

The indazole compounds described above include the compounds themselves, as well as their salts, prodrugs, and solvates, if applicable. A salt, for example, can be formed between an anion and a positively charged group (e.g., amino) on a indazole compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a indazole compound. Suitable cations include sodium ion, potassium ion, magnesium ion, calcium ion, and an ammonium cation such as tetramethylammonium ion. The indazole compounds also include those salts containing quaternary nitrogen atoms. Examples of prodrugs include esters and other pharmaceutically acceptable derivatives, which, upon administration to a subject, are capable of providing active indazole compounds. A solvate refers to a complex formed between an active indazole compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the indazole compounds described above for use in treating cancer, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are 55 exemplary compounds of this invention:

Compound 1

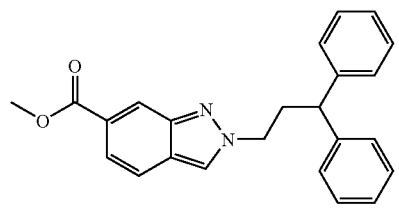

Compound 2

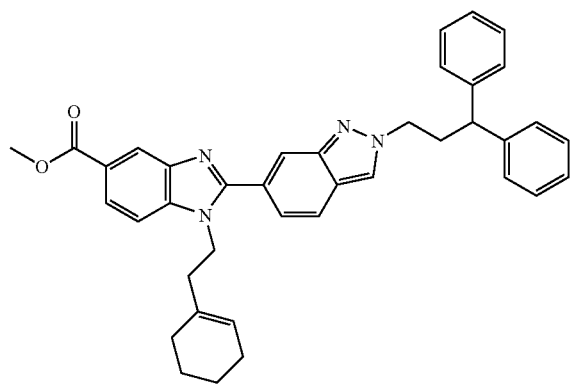

Compound 3

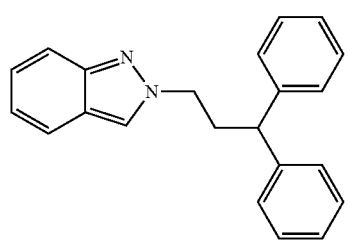

Compound 4

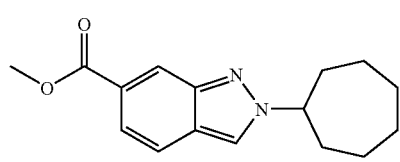

-continued
Compound 5
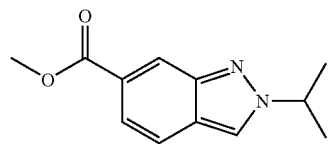
Compound 6
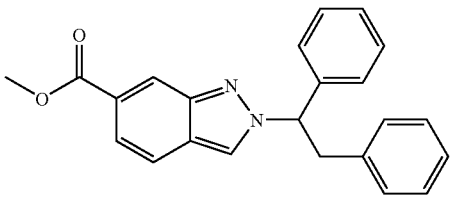
Compound 7
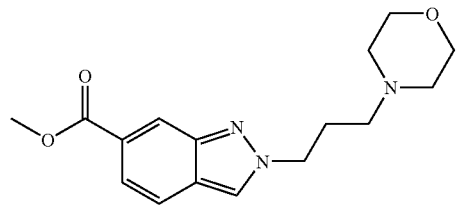
Compound 8
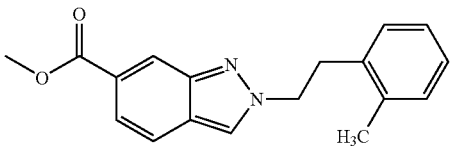
Compound 9
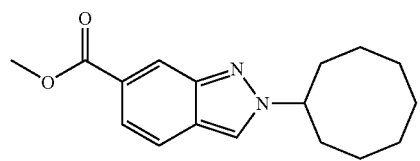
Compound 10
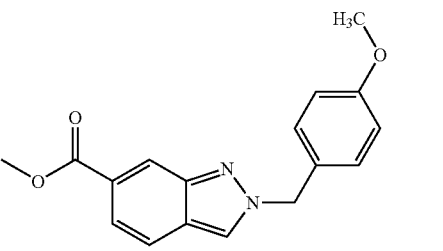
Compound 11
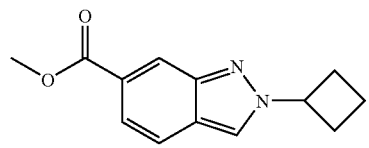
Compound 12
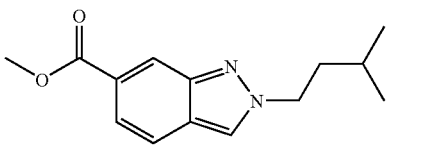
Compound 13
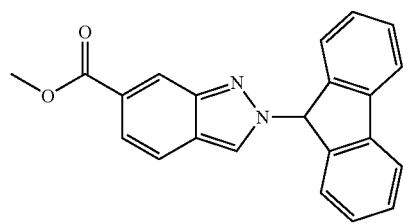
Compound 14
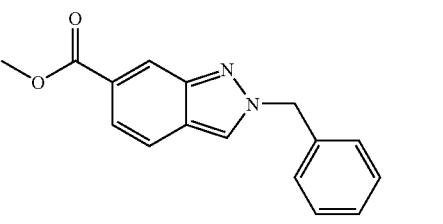
Compound 15
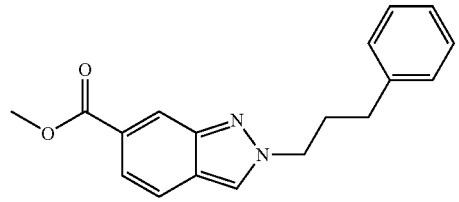
Compound 16
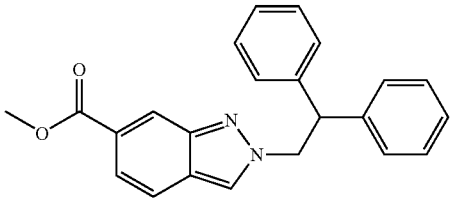
Compound 17
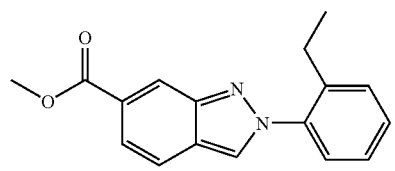
Compound 18
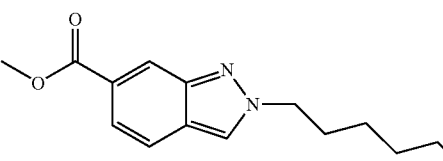

-continued
Compound 19
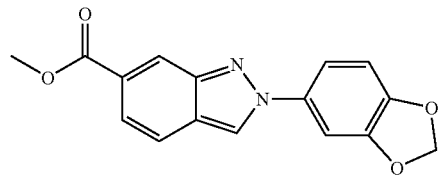
Compound 20
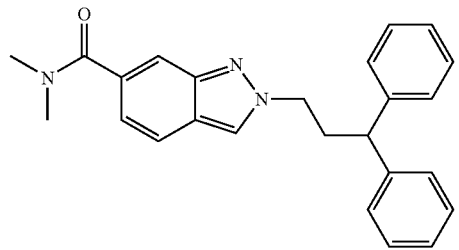
Compound 21
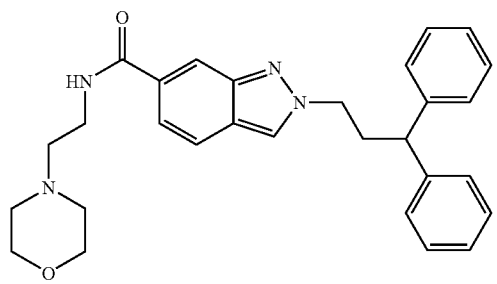
Compound 22
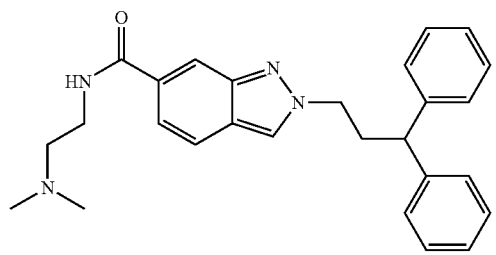
Compound 23
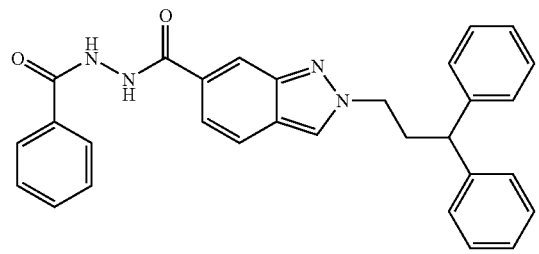
Compound 24
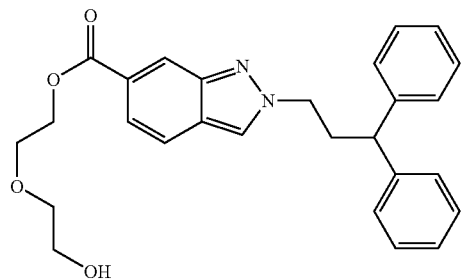
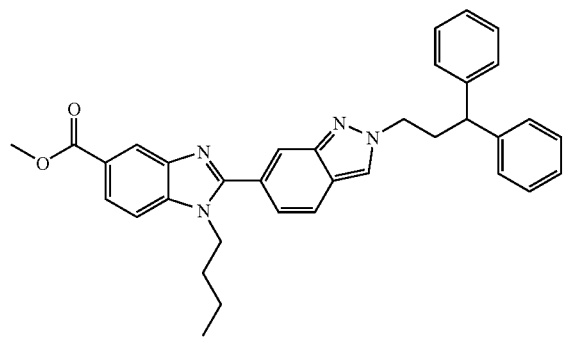
Compound 26
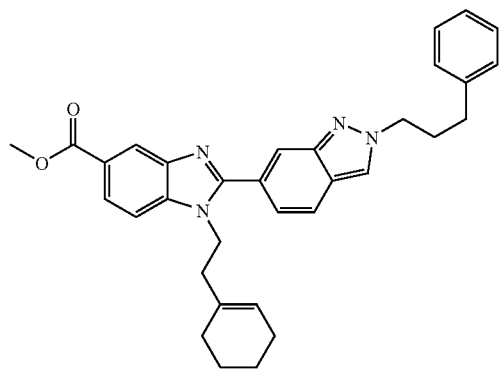

-continued
Compound 27
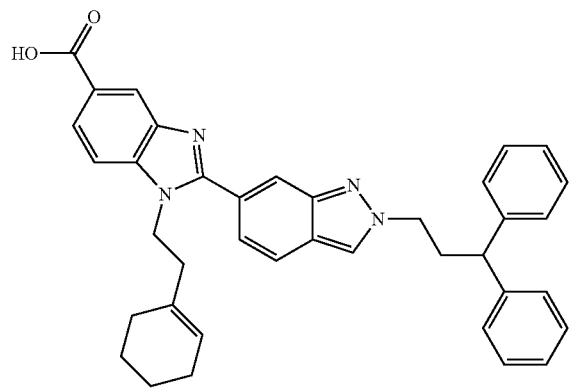
Compound 28]
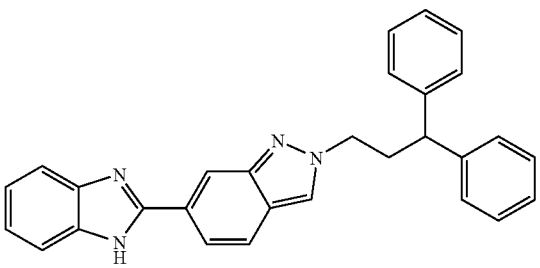
Compound 29
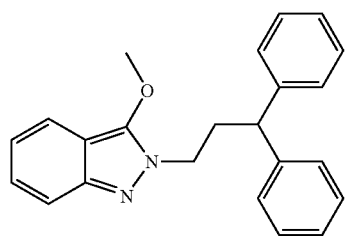
Compound 30
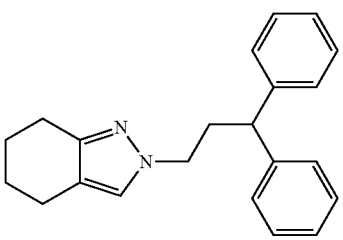
Compound 31
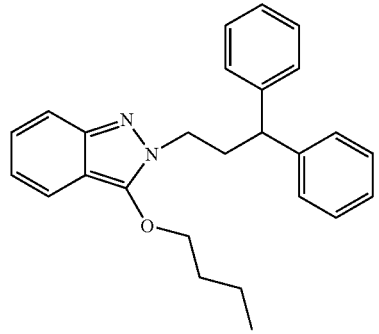
Compound 32
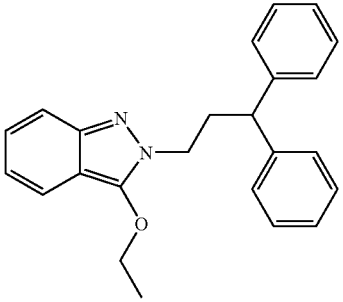
Compound 33
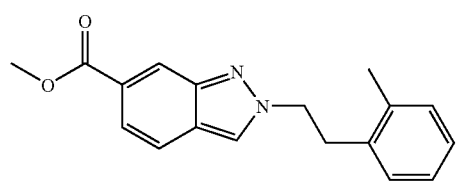
Compound 34
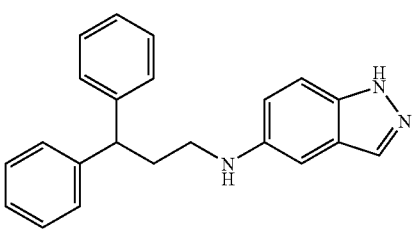
Compound 35
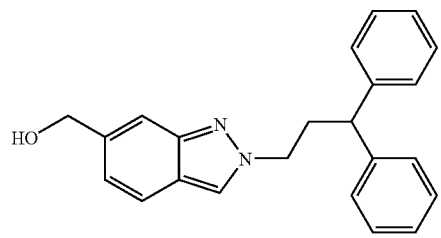
Compound 36
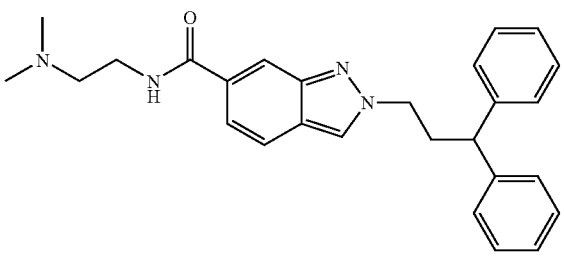

-continued
Compound 37
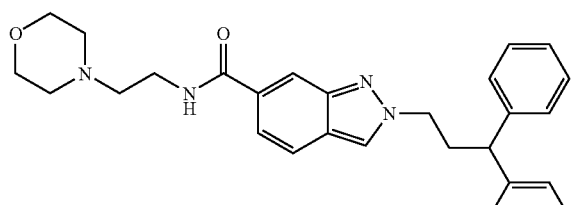
Compound 38
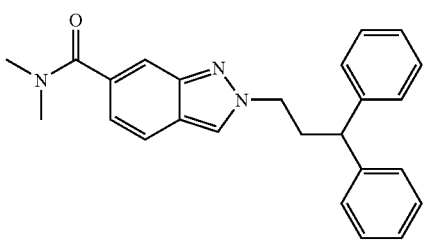
Compound 39
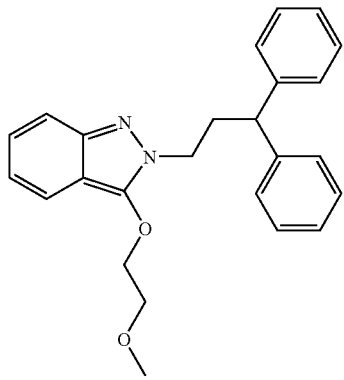
Compound 40
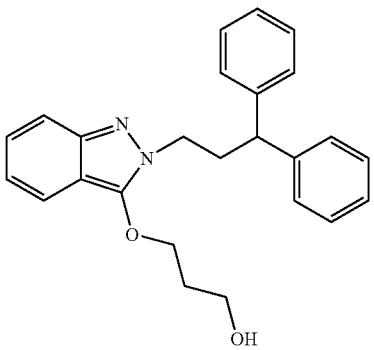
Compound 41
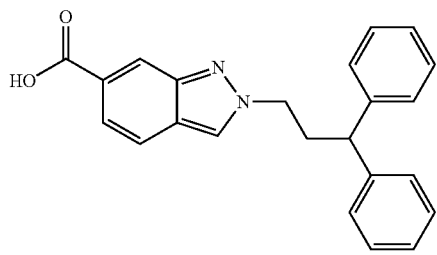
Compound 42
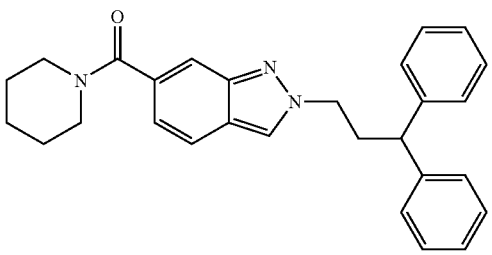
Compound 43
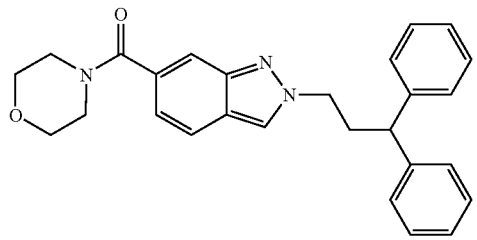
Compound 44
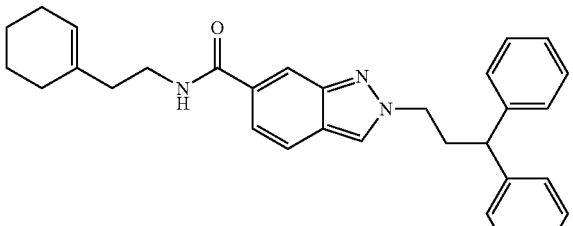
Compound 45
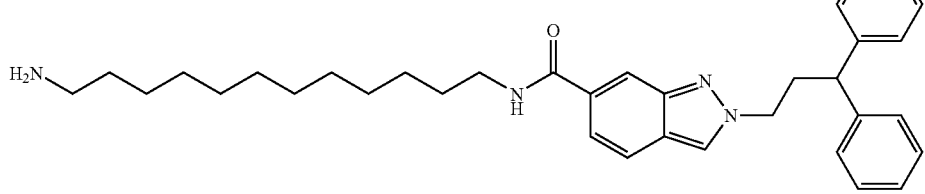

-continued
Compound 46
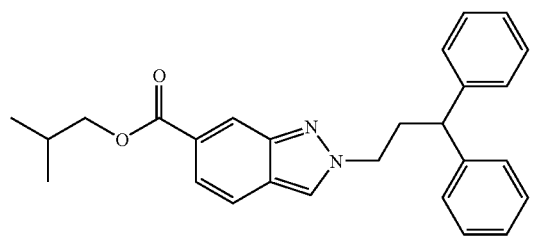
Compound 47
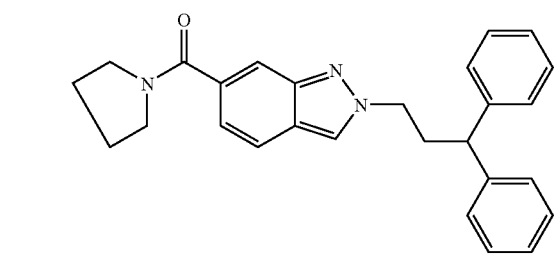
Compound 48
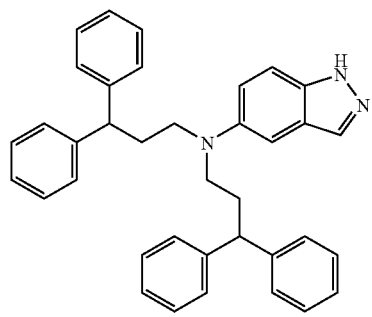
Compound 49
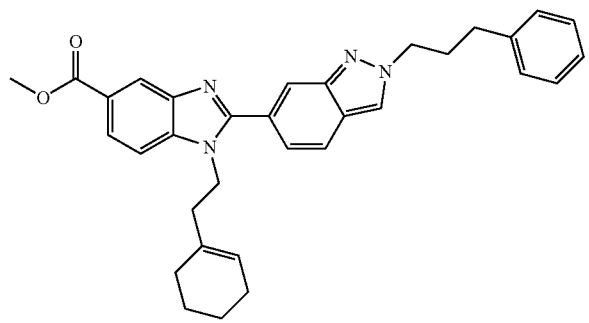
Compound 50
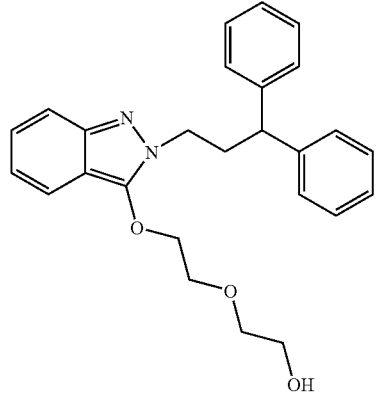
Compound 51
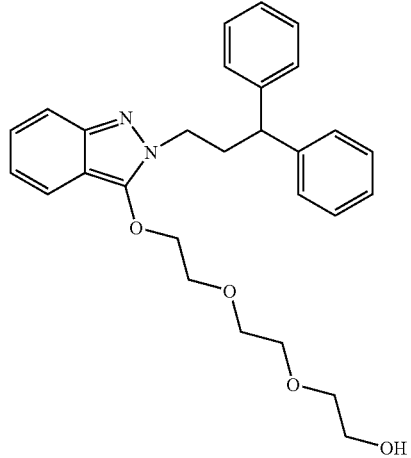
Compound 52
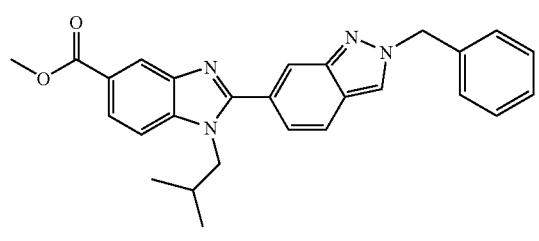
Compound 53
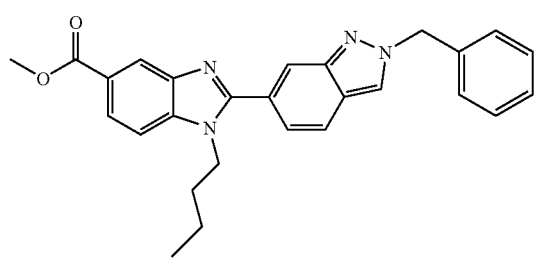

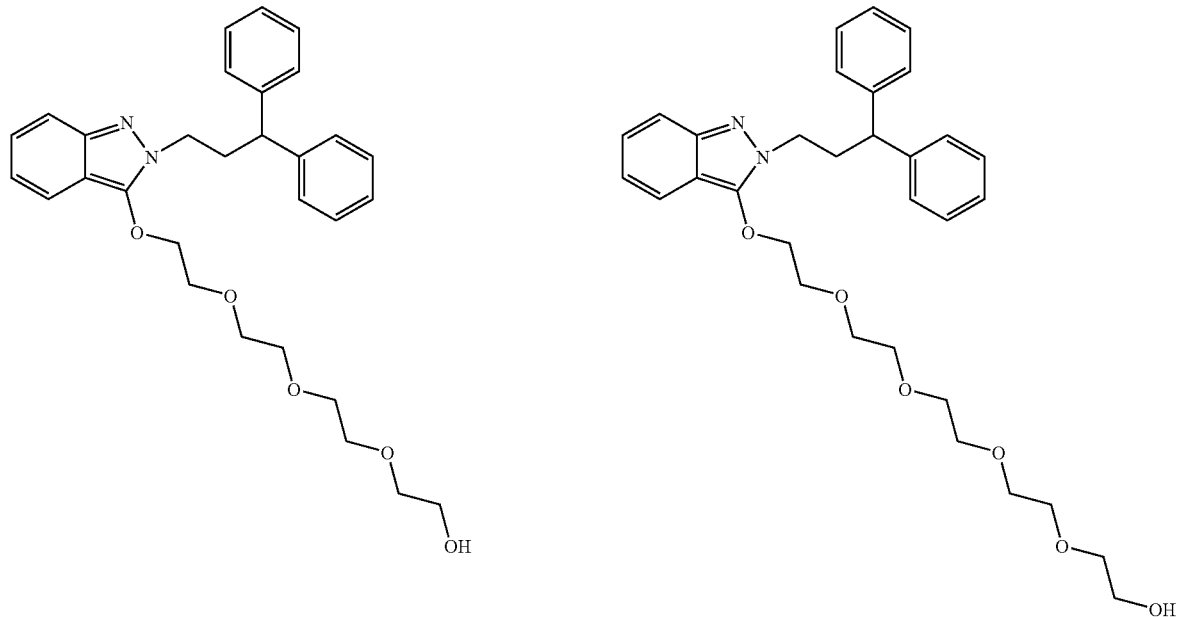

Compound 54

Compound 55

The indazole compounds described above can be prepared by methods well known in the art. Examples 1-55 below provide detailed descriptions of how compounds 1-55 were actually prepared.

Scheme I shown below illustrates a typical synthetic route for synthesizing certain exemplary indazole compounds. $R_2$ and $R_5$ in this scheme can be those described in the Summary section above.

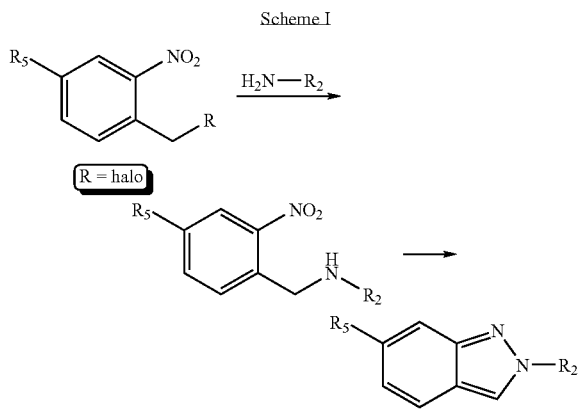

Scheme I

Specifically, as shown in Scheme I above, a substituted benzene containing a nitro group and a halo group can first react with a primary amine compound to form a secondary amine compound. This compound can then undergo a ring closure reaction between the nitro group and the secondary amino group to form an indazole compound of this invention.

An indazole compound synthesized above can be purified by a suitable method such as column chromatography, high-pressure liquid chromatography, or recrystallization.

Other indazole compounds can be prepared using other suitable starting materials through the above synthetic routes and others known in the art. The methods described above may also additionally include steps, either before or after the steps described specifically herein, to add or remove suitable protecting groups in order to ultimately allow synthesis of the indazole compounds. In addition, various synthetic steps may be performed in an alternate sequence or order to give the desired compounds. Synthetic chemistry transformations and protecting group methodologies (protection and deprotection) useful in synthesizing applicable indazole compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The indazole compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing at least one indazole compound described above and a pharmaceutical acceptable carrier. Further, this invention covers a method of administering an effective amount of one or more of the indazole compounds to a patient having cancer. "An effective amount" refers to the amount of an active indazole compound that is required to confer a therapeutic effect on the treated subject. Effective doses will vary, as recognized by those skilled in the art, depending on the types of diseases treated, route of administration, excipient usage, and the possibility of co-usage with other therapeutic treatment. For example, a daily dose of 5 mg/kg of compound 1 can be used reduce metastasis and a daily dose of 50 mg/kg can be used to inhibit tumor growth.

To practice the method of the present invention, a composition having one or more indazole compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active indazole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active indazole compound. Examples of other carriers include colloidal silicon oxide, magnesium stearate, cellulose, sodium lauryl sulfate, and D&C Yellow # 10.

The indazole compounds described above can be preliminarily screened for their efficacy in treating above-described diseases by in vitro and in vivo assays (see Examples 56 and 57 below) and then confirmed by clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

Preparation of Compound 1 methyl 2-(3,3-diphenylpropyl)-2H-indazole-6-carboxylate

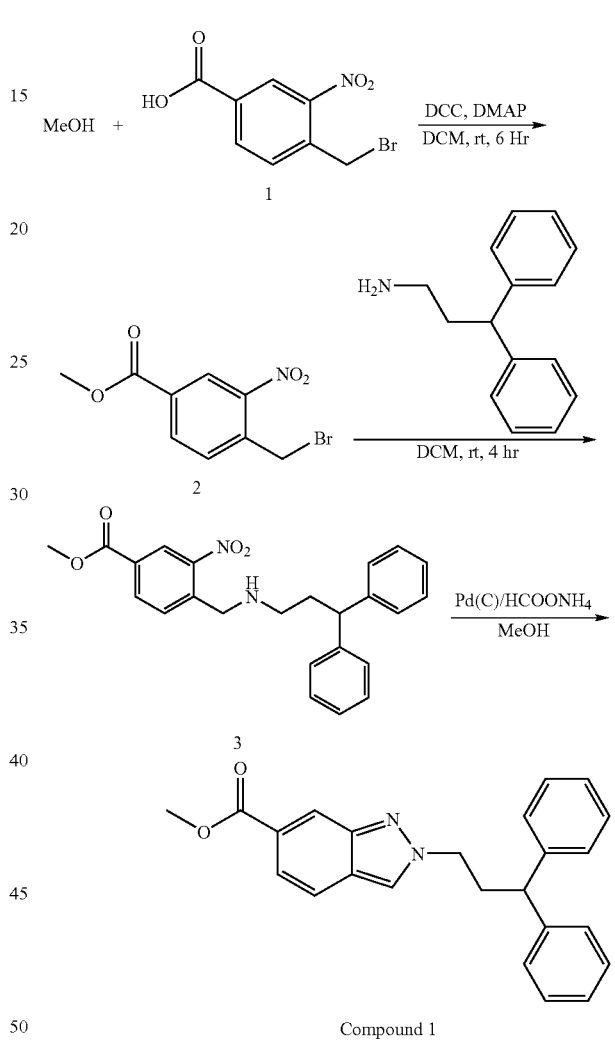

Compound 1

A solution of dicyclohexylcarbodiimide (DCC, 0.95 g, 4.61 mmol, 1.2 equiv) in 10 mL of dichloromethane (DCM) was added dropwise to a stirred mixture of 4-bromomethyl-3-nitro-benzoic acid 1 (1.0 g, 3.84 mmol, 1.0 equiv) and 4-dimethylaminomethylpyridine (DMAP) (0.020 g, 0.19 mmol, 0.05 equiv) in 10 mL of dichloromethane-methanol (10%) at room temperature. The mixture was stirred for 6 hours to obtain 4-bromomethyl-3-nitro-benzoic acid methyl ester 2. Dicyclohexyl urea (DCU) thus obtained was removed by filtration and the solvent in the filtered solution was removed under vacuum. The residue was purified by column chromatography using hexane-ethyl acetate (15%) as an eluant to give ester 2 as a light yellow oil.

To a solution of ester 2 (0.91 g, 3.32 mmol, 1.0 equiv) in 10 mL of dichloromethane was added dropwise 3,3-diphenylpropylamine (1.40 g, 6.64 mmol, 2.0 equiv). The mixture was stirred at room temperature for 8 hours. After the amine salt thus obtained was removed by filtration, the solvent in the filtered solution was removed under vacuum to give crude 4-[(3,3-diphenyl-propylamino)-methyl]-3-nitro-benzoic acid methyl ester 3. The crude product was purified by column chromatography using hexane-ethyl acetate (25%) to give ester 3 as a light brown oil.

4-[(3,3-diphenyl-propylamino)-methyl]-3-nitro-benzoic acid methyl ester 3 (0.81 g, 3.21 mmol) was dissolved in 10 ml of methanol and treated with ammonium formate (1.26 g, 20.02 mmol, 10 equiv) and palladium on carbon (162 mg, 20%). The mixture was stirred for 1 day at room temperature. After the mixture was then filtered through a small plug of Celite and washed with dichloromethane, the solvent was removed under vacuum to give a crude product. The crude product was purified by column chromatography using hexane-ethyl acetate (25%) to give compound 1,2-(3,3-diphenyl-propyl)-2H-indazole-6-carboxylic acid methyl ester, as a white solid.

$^1$H NMR (300 MHz, CDCl$_3$) δ 8.53 (s, 1H), 7.82 (s, 1H), 7.75~7.72 (dd, J=8.7, 1.2 Hz, 1H), 7.69~7.66 (dd, J=8.7, 0.5 Hz, 1H), 7.35~7.20 (m, 10H), 4.41 (t, J=6.9 Hz, 2H), 3.97 (s, 3H), 3.88 (t, J=7.9 Hz, 1H), 2.87~2.80 (q, J=7.2 Hz, 2H).

$^{13}$C NMR (75 MHz, CDCl3) δ 167.56, 148.13, 143.25, 128.68, 127.71, 126.61, 123.65, 123.27, 121.28, 121.18, 120.07, 52.36, 52.13, 48.12, 35.94; IR (cm-1, neat): 3236, 2948, 1713, 1601, 1443, 1269.

MS (EI): m/z 370 (M$^+$). Exact mass calculated for $C_{24}H_{22}N_2O_2$: m/z 370.1681 Found 370.1681.

EXAMPLES 2-55

Preparation of Compounds 2-55

Compounds 2-55 were prepared in a manner similar to that described in Example 1.

EXAMPLE 56

KIRA-ELISA Assay

This assay was performed in two microtiter plates. The first plate was used to culture an adherent cell line expressing the VEGF receptor 3 and to stimulate the receptor with a test compound. The second plate was used to capture the solubilized membrane receptor, which was then probed for phosphotyrosine content with phosphotyrosine-specific antibody.

Specifically, H928 cells (2×10$^5$) in 100 µl medium were added to each well in a flat-bottom 24-well culture plate and cultured overnight at 37° C. in 5% CO$_2$. After the supernatants were removed, the cells were serum-starved for 24 hours. A medium containing a test compound was added into each well and the cell culture was incubated for 30 minutes before it was stimulated by recombinant VEGF-C for 15 minutes. After the supernatants were removed, 100 µl of a lysis buffer were added into each well to lyse the cells and solubilize the VEGFR3. The lysis buffer included 150 mM NaCl containing 50 mM Hepes (Genentech media prep), 0.5% Triton-X 100 (Genentech media prep), 0.01% thimerosol, 30 kIU/ml aprotinin (ICN Biochemicals, Aurora, Ohio), 1 mM 4-(2-aminoethyl)benzenesulfonyl fluoride hydrochloride (AEBSF; ICN Biochemicals), and 2 mM sodium orthovanadate. The plate was then put on a plate shaker (Bellco Instruments Vineland, N.J.) and the substance in each well of the plate underwent mixing for 60 minutes at room temperature. While the cells were being solubilized, an ELISA microtiter plate (Nunc Maxisorp, Inter Med, Denmark) coated overnight at 4° C. with the affinity-purified polyclonal anti-VEGFR 3 (2.5 µg/ml in phosphate buffered saline (PBS), 100 µl/well) were decanted, tamped on a paper towel, and blocked with 150 µl/well block buffer (PBS containing 0.5% BSA and 0.01% thimerosol) for 60 minutes at room temperature with gentle agitation. The anti-VEGFR 3-coated plate was subsequently washed twice with a wash buffer (PBS containing 0.05% Tween 20 and 0.01% thimerosol). The lysate containing solubilized VEGFR 3 from the cell-culture microtiter well were transferred (85 µl/well) to the anti-VEGFR 3-coated ELISA plate and incubated for 2 hours at room temperature with gentle agitation. The unbound receptors were removed by washing with a wash buffer. 100 µl of biotinylated 4G10 (antiphosphotyrosine) diluted to 0.2 µg/ml in dilution buffer (PBS containing 0.5% BSA, 0.05% Tween 20, 5 mM EDTA, and 0.01% thimerosol) were added into each well. After incubation for 2 hours at room temperature, the plate were washed and 100 µl HRP-conjugated streptavidin (Zymed Laboratories, S. San Francisco, Calif.) diluted 1:2000 in dilution buffer will be further added. After the free avidin conjugate were washed away, 100 µl freshly prepared substrate solution (tetramethyl benzidine, TMB) was added to each well. The reaction was allowed to proceed for 10 minutes and the color development was stopped by the addition of 100 µl/well 1.0 M H$_3$PO$_4$. The absorbance at 450 nm and the absorbance at a reference wavelength of 650 nm ($A_{450/650}$) were measured using an ELISA reader.

The inhibition efficacy of each test compound is expressed as an inhibition percentage calculated according to the following formula: 1-[(C−A)/(B−A)]. In this formula, A is the basal amount of phosphotyrosine detected in a blank control, B is the amount of phosphotyrosine detected with VEGF-C only, and C is the amount of phosphotyrosine detected with a test compound and VEGF-C.

Among the 55 compounds, 50 compounds (i.e., compounds 1-22, 24-30, 32, 34-39, 41-50, and 52-55) were tested. Unexpectedly, 46 of the test compounds showed more than 20% inhibition of VEGF receptor 3. Among the 46 compounds, 24 showed more than 50% inhibition, and 5 showed more than 75% inhibition.

EXAMPLE 57

In Vivo Assay

Compound 1 was tested for its efficacy in inhibiting tumor growth on murine tumor xenografts. Briefly, VEGF-C overexpressing H928 cells or LLC were trypsinized, washed with PBS and resuspended in PBS. The concentration was adjusted to 3×10$^6$ cells/100 µl in PBS. The cell suspension was then injected subcutaneously into the right abdominal wall of C57BL/6J mice (7-8 week old, one tumor per mice). When the diameter of implanted tumor cells reached 5 mm, compound 1 or vehicle was administered intraperitoneally once daily. The length and width of the tumor was measured every 2-3 days by using a caliper. The tumor volume was then calculated as follows: volume=length×width$^2$×0.52. Student's t test was used to compare tumor volumes, with P<0.05 being considered significant. After 8 weeks, the mice were sacrificed in a CO$_2$ chamber and the tumors were collected. Lungs and lymph nodes were removed. For tumor metastasis assay (Quantitative analysis of lung metastatic nodules), the number of lung tumor nodule was counted under a dissecting microscope. Compound 2 was tested by the same procedure.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

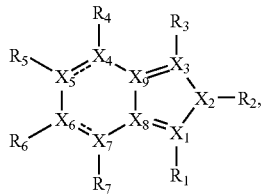

(I)

wherein
each ═ independently is a double bond;
each of $X_1$, $X_4$, $X_5$, $X_6$, $X_7$, $X_8$, and $X_9$, independently, is C, and each of $X_2$ and $X_3$, independently, is N;
each of $R_1$, $R_2$, $R_3$, $R_4$, $R_5$, $R_6$, and $R_7$, independently, is H, $C_1$-$C_{10}$ alkyl, or $COOR_a$, in which $R_a$ is H or $C_1$-$C_{10}$ alkyl; and
$R_2$ is $C_4$, $C_7$, or $C_8$ cycloalkyl.

2. The compound of claim 1, wherein $R_1$ is $H_a$.

3. The compound of claim 1, wherein the compound is

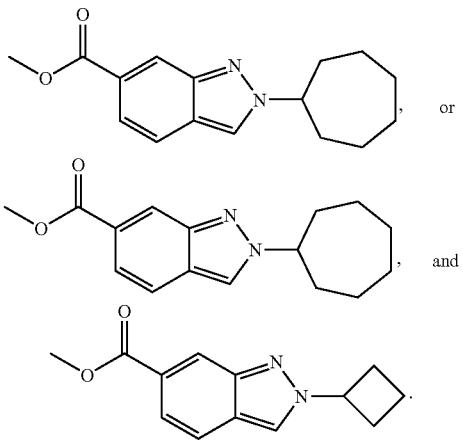

* * * * *